United States Patent [19]
Chin et al.

[11] Patent Number: 5,425,375
[45] Date of Patent: Jun. 20, 1995

[54] REUSABLE MEDICAL DEVICE WITH USAGE MEMORY, SYSTEM USING SAME

[75] Inventors: Donald Chin; Mir A. Imran, both of Palo Alto, Calif.

[73] Assignee: Cardiac Pathways Corporation, Sunnyvale, Calif.

[21] Appl. No.: 119,973

[22] Filed: Sep. 9, 1993

[51] Int. Cl.6 .............................................. A61B 5/00
[52] U.S. Cl. ................................ 128/736; 374/142; 374/208; 364/557
[58] Field of Search ............... 128/672, 673, 675, 713, 128/692, 662.03, 662.09; 374/142, 208, 104, 141, 151, 163, 184; 364/557

[56] References Cited
U.S. PATENT DOCUMENTS

| | | |
|---|---|---|
| 1,397,313 | 11/1921 | Copelli et al. |
| 1,455,268 | 5/1923 | Sapienza . |
| 2,391,309 | 12/1945 | Harriott . |
| 4,303,984 | 12/1981 | Houvig .................... 364/571 |
| 4,407,298 | 10/1983 | Lentz et al. ................ 128/713 |
| 4,418,392 | 11/1983 | Hata ......................... 364/571 |
| 4,858,615 | 8/1989 | Meinema .................... 128/672 |
| 4,868,476 | 9/1989 | Respaut ..................... 318/632 |
| 4,986,276 | 1/1991 | Wright .................... 128/662.04 |
| 5,018,874 | 5/1991 | Weynant née Girones . |
| 5,046,505 | 9/1991 | Sekii et al. .................. 128/713 |

Primary Examiner—William E. Kamm
Assistant Examiner—Robert L. Nasser, Jr.
Attorney, Agent, or Firm—Flehr, Hohbach, Test, Albritton & Herbert; Edward N. Bachand

[57] ABSTRACT

A reusable medical device for performing an operation on a body. The device includes a flexible elongate member having proximal and distal extremities. The distal extremity is adapted to be inserted into the body for performing the operation therein and the proximal extremity is adapted to be disposed outside the body. At least one sensor for sensing a parameter relating to each use of the medical device and generating an electrical signal with respect to each use is provided. At least one memory device is carried by the proximal extremity for recording information relating to the use of the medical device to aid in determining whether the medical device is within warranty. A method is provided for determining usage of the medical device and includes the steps of sensing a parameter relating to each use of the medical device, noting the time at which use of the device is sensed and recording information relating to the use on the memory device to aid in determining whether the medical device is within warranty.

12 Claims, 3 Drawing Sheets

REUSABLE MEDICAL DEVICE WITH USAGE MEMORY, SYSTEM USING SAME

This invention pertains generally to reusable medical devices and, more particularly, to medical devices with usage memories.

Many reusable medical devices, such as mapping, ablation or angioplasty catheters, have a finite lifetime based on usage after which they may fail or become inoperable. In the case of a catheter, for example, the active components such as the plastic tubing or basket arms may fail after excessive usage. The life of these devices, however, has been found to be more a function of the usage cycles or number of procedures than the cumulative usage time. This is in part due to the sterilizing and other wear inducing procedures performed on the device between each operational use. Because of the foregoing, there is a need for a new and improved medical device which overcomes the above named disadvantages.

In general, it is an object of the present invention to provide a method and device for automatically monitoring use of a reusable medical device.

Another object of the invention is to provide a method and device such as described above wherein the number of uses is automatically recorded on the device.

Another object of the invention is to provide a method and device such as described above wherein the usage information is retained on the device when power thereto is shut off.

Another object of the invention is to provide a method and device such as described above which can distinguish between usage cycles and operational steps during a usage cycle.

Additional objects and features of the invention will appear from the following description from which the preferred embodiments are set forth in detail in conjunction with the accompanying drawings.

Figure 1:
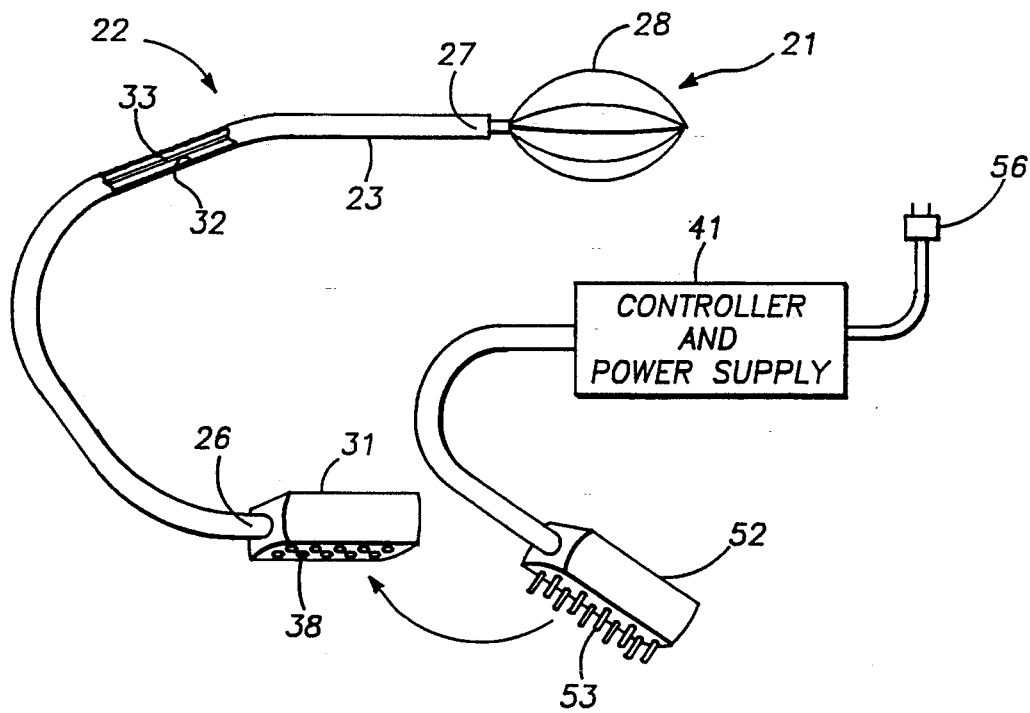
FIG. 1 is a perspective view of a medical device with usage memory of the present invention.

In general, the reusable medical device of the invention is for performing an operation on a body and comprises a flexible elongate member having proximal and distal extremities. The distal extremity is adapted to be inserted into the body for performing the operation therein and the proximal extremity is adapted to be disposed outside the body. At least one sensing means for sensing a parameter relating to each use of the medical device and generating an electrical signal with respect to said each use is provided. Recording means is carried by the proximal extremity for recording information relating to said use of the medical device to aid in determining whether the medical device is within warranty. A method is provided for determining usage of the medical device and includes the steps of sensing a parameter relating to each use of the medical device, noting the time at which use of the device is sensed and recording information relating to said use on the recording means to aid in determining whether the medical device is within warranty.

More particularly, medical system 21 of the present invention can include a reusable medical device or apparatus for performing an operation or procedure in a human body in the form of a reusable and disposable catheter probe 22 of the type disclosed in U.S. Pat. No. 5,156,151 and copending application Ser. No. 08/044,255 filed Apr. 7, 1993. As disclosed therein and illustrated in FIG. 1, catheter probe 22 includes a flexible elongate tubular member 23 formed from a suitable material such as plastic which is circular in cross section. Tubular member 23 has a first or proximal extremity 26 adapted to be inserted into a human body for performing an operation on the body and a second or distal extremity 27 adapted to be disposed outside of the body to permit access to and operation of catheter probe 22.

A basket assembly 28 which utilizes electrical energy is carried by catheter distal extremity 27 and an electrical connector 31 is secured to catheter proximal extremity 26. Tubular member 23 is provided with at least one lumen 32 formed therein and extending from proximal extremity 26 to distal extremity 27. Lead means for carrying electrical energy from the proximal to the distal extremities of catheter probe 22 is carried within lumen 32 and includes electrical wire 33.

Figure 2:
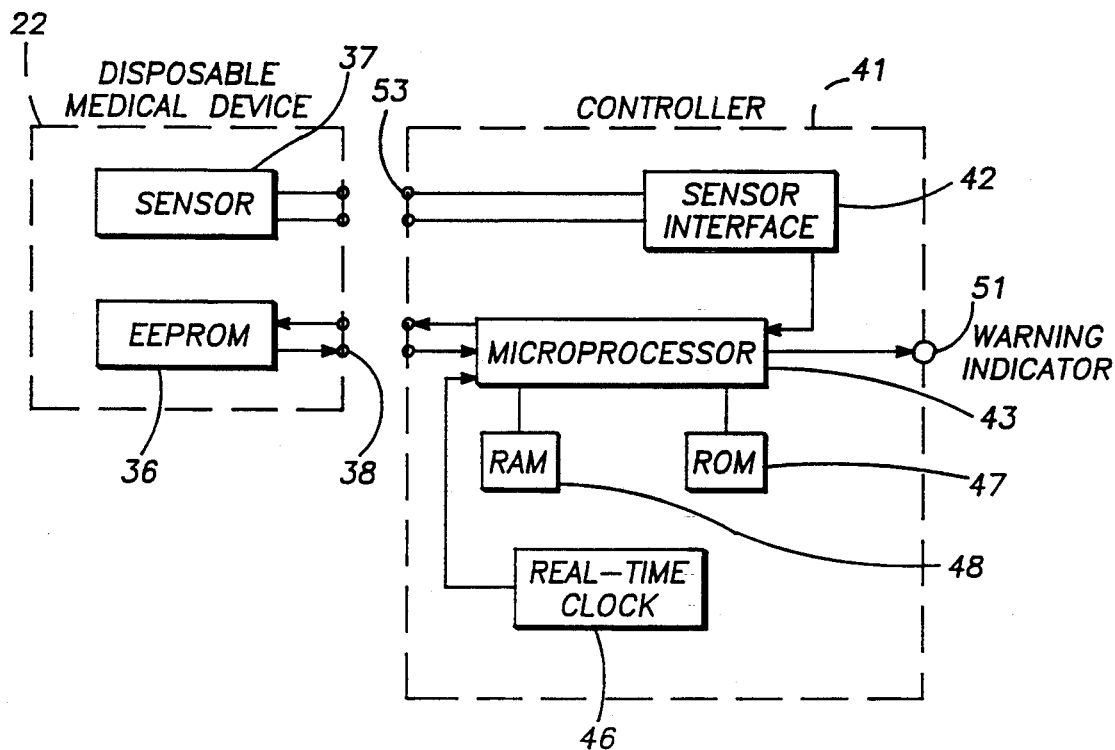
FIG. 2 is a block diagram of the medical device with usage memory shown in FIG. 1.
Figure 3:
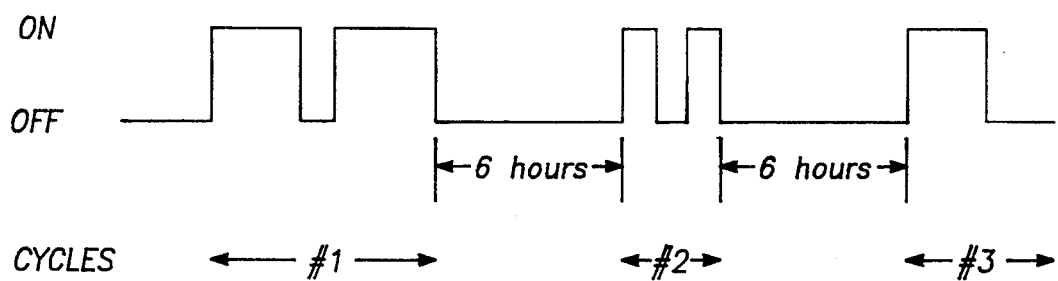
FIG. 3 is an operation diagram of the medical device with usage memory shown in FIG. 1.

Catheter probe 22 includes at least one memory device or memory means permanently attached thereto for recording usage of the probe. A suitable alterable memory means such as an electrical erasable programmable read-only memory unit 36 (EEPROM), of the type manufactured by Xicor of Milpitas, Calif., is housed in first connector 31 (See FIG. 2). As appreciated by those skilled in the art, EEPROM 36 is a nonvolatile writable memory unit and, as such, retains information written thereto when power thereto is turned off. Connector 31 further includes at least one sensing or sensor means, and as shown in FIG. 2 one sensing means in the form of electrical sensor 37, for detecting when probe 22 is in operation. Electrical sensor 37 senses electrical current passing through electrical wire 33 from catheter proximal extremity 26 to catheter distal extremity 27. EEPROM 36 and electrical sensor 37 can be carried elsewhere on catheter probe 22 and be within the scope of the present invention.

Electrical connector 37 is formed with a plurality of sockets 38 which are electrically connected to EEPROM 36 and electrical sensor 37 and are included within the first junction means of medical system 21 which permits making electrical contact with catheter probe 22.

A controller and power supply 41 forms part of medical system 21 and includes a sensor interface 42, a microprocessor 43 and a real time clock 46 (See FIGS. 1 and 2). Sensor interface 42 and clock 46 each have outputs electrically connected to inputs to microprocessor 43. A read only memory 47 (ROM), to hold the algorithm performed by microprocessor 43, and a random access memory 48 (RAM), for operation of the algorithm, are electrically connected to microprocessor 43 for use therewith. Controller 41 further includes an overuse warning indicator 51 having an input electrically connected to an output of microprocessor 43.

Controller 41 is provided with second junction means, in the form of second electrical connector 52, which includes a plurality of pins 53 for making a nonpermanent electrical connection with catheter probe 22. Pins 53 are configured to cooperatively mate with sockets 38 and are electrically connected to sensor interface 42 and microprocessor 43. Controller 41 has a plug 56 for connecting the controller to a conventional power source of 110 volts at 60 hertz.

Microprocessor 43 and clock 46 are included within the evaluation means for determining the number of sustained one-time uses of catheter probe 22. In general, microprocessor 43 compares the time at which sensor 37 detects electrical energy being supplied to catheter probe 22 against the time sensor 37 previously detected electrical energy being supplied to probe 22. Microprocessor records a usage cycle for catheter probe 22 every time the catheter probe is activated and operated following a predetermined period of six hours.

Figure 4:
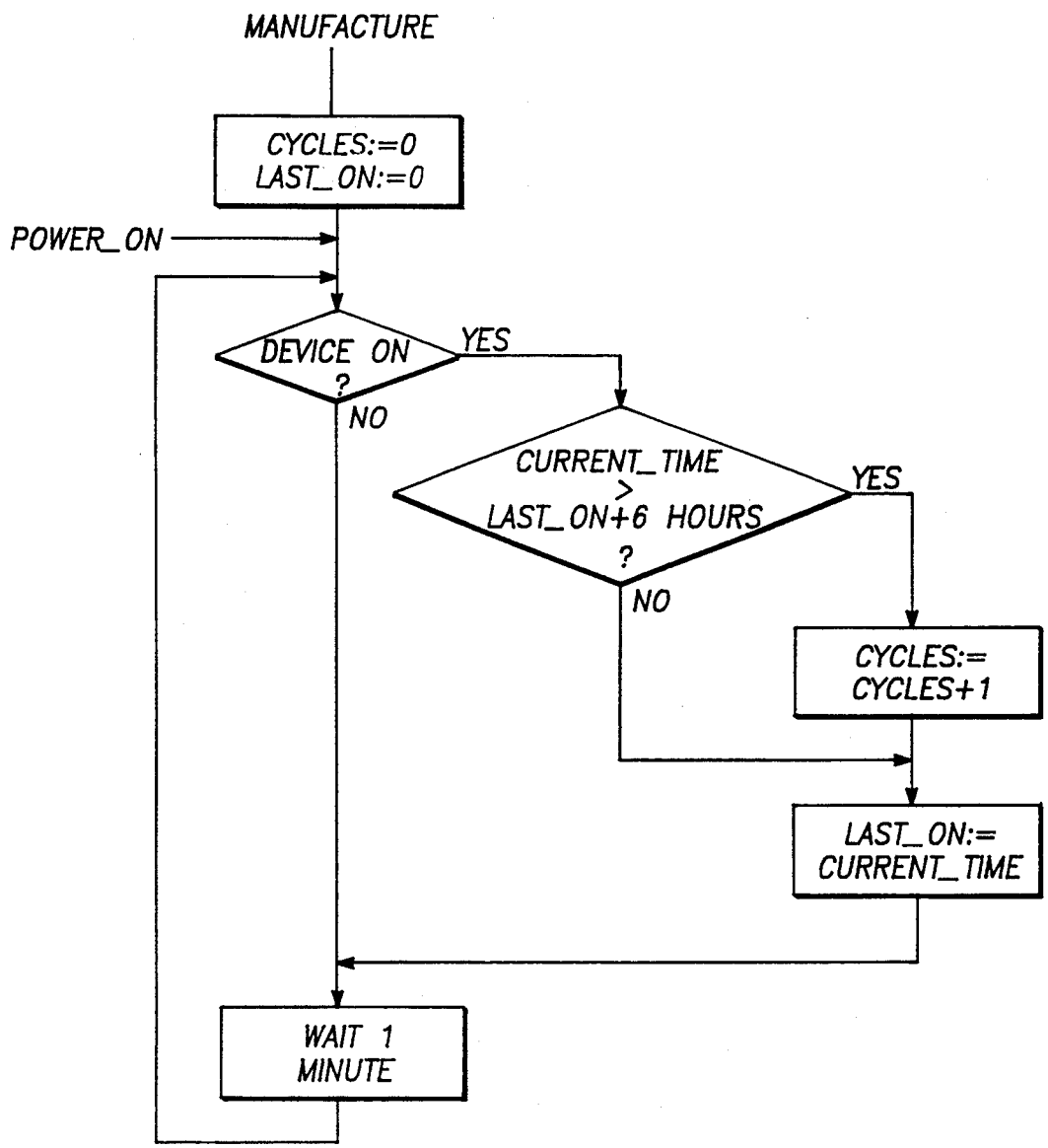
FIG. 4 is a flow chart of the medical device with usage memory shown in FIG. 1.

The methods steps performed by microprocessor 43 for determining usage cycles or cycles of operation of catheter probe 22 is more fully set forth in FIG. 4. During manufacture of catheter probe 22, two integer variables labeled "cycles" and "last_on" are cleared to zero and stored in EEPROM 36. Once catheter distal extremity 27 has been inserted into the human body to commence a procedure and has been properly positioned therein, catheter connector 31 is coupled to controller 41 and electrical current from plug 56 is supplied to controller 41 and catheter probe 22 to enable operation thereof. Activating controller 41 automatically powers microprocessor 43 and permits electrical current to be transmitted through pins 53, sockets 38 and electrical wire 33 for operation of basket assembly 28 carried by catheter distal extremity 27. Once microprocessor 43 is powered, it commences polling electrical sensor 37 at predetermined one minute intervals for information. The microprocessor determines when the one minute interval has elapsed through information received by it from clock 46. Sensor 37 detects when electrical current is supplied to catheter probe 22 from controller 41. If at the time of polling basket assembly 28 is not in operation and electrical current is not passing through electrical wire 33, microprocessor 43 waits the predetermined one minute interval and then polls electrical sensor 37 again.

If the polling information received by microprocessor 43 from sensor 37 indicates that basket assembly 28 is in operation, the microprocessor performs additional method steps to determine whether a cycle of operation has occurred. Microprocessor 43 compares the time of polling, which equals the current time, to the "last_on" integer. If the time interval between the current time and the "last_on" integer is greater than six hours, microprocessor 43 increments the "cycles" integer by one, changes the "last_on" integer to the current time, and stores the "cycles" and "last_on" integers in EEPROM 36. For the first use of catheter probe 22, the time interval between the current or polling time and the time recorded in EEPROM 36 by the "last_on" integer will exceed six hours and, as a result, microprocessor 43 will increment the "cycles" integer by one. If said time interval is less than six hours, microprocessor 43 does not increment the "cycles" integer, but changes the "last_on" integer to the current time and stores the revised "last_on" integer in EEPROM 36. Microprocessor 43 then waits the predetermined one minute interval and polls electrical sensor 37 again to repeat the polling cycle illustrated in FIG. 4. Once the "cycles" integer exceeds a predetermined number of usage cycles recorded in EEPROM 36, microprocessor 43 activates overusage warning indicator 51, which can be any suitable indicator such as a warning light or buzzer.

The predetermined time interval by which the current time or polling time must exceed the "last_on" integer for microprocessor 43 to record a usage cycle is greater than the continuous time interval or period during which catheter probe 22 is generally nonoperational for a continuous period of time during a procedure. As can be appreciated by those skilled in the art, electrical current may be cut off to electrical wire 33 to render basket assembly 28 inoperable one or more times during any particular operation or procedure involving catheter probe 22. Electrical current may be cut off intentionally, for example to move catheter probe distal extremity 27 and basket assembly 28 thereon to another location or position within the body, or unintentionally, for example as a result of a power shut down.

Should such an electrical cut off occur and catheter probe 22 is thereafter reactivated before a time period of six hours has elapsed, microprocessor 43 will not record a usage cycle. More specifically, once basket assembly 28 is reactivated, microprocessor 43 enters the polling loop illustrated in FIG. 4. The "last_on" integer stored in EEPROM 36 is the previous polling time which occurred within the minute of operation immediately preceding the time at which current was cut off. Since the current time or polling time does not exceed that "last_on" integer by six hours, the "cycles" integer is not incremented to indicate another usage cycle.

The predetermined interval of six hours also approximates the time period required to sterilize, clean and otherwise reasonably prepare catheter probe 22 between operations and procedures. It should be appreciated that the predetermined interval for determining a usage cycle may be other than six hours and be within the scope of the present invention.

The polling interval of microprocessor 43 must be long enough to ignore brief and irrelevant power or electrical shut downs but short enough to provide sufficient accuracy to the determination of usage cycles by microprocessor 43. Although the polling interval is stated and shown as one minute, other polling intervals may be chosen and be within the scope of the present invention.

As discussed above, EEPROM 36 is permanently attached to catheter probe 22 so that the history of the probe remains associated therewith. The information stored on EEPROM 36, including the "last_on" and "cycles" integer, can be easily accessed therefrom by connecting catheter probe 22 to a controller 41. If the "cycles" integer exceeds the maximum number of usage cycles recommended by the manufacturer, warning indicator 51 is activated to alert the user of catheter probe 22. Furthermore, this information is retained by EEPROM 36 after power thereto is shut off and allows a manufacturer to easily determine whether catheter probe 22 has been used within warranty as to the number of permitted usages thereof. The stored information can also assist the manufacturer in analyzing the effects of probe usage, including its relationship to effectiveness, failure and usage life.

It should be appreciated that pressure or other nonelectrical sensing devices can be used as sensor means and be within the scope of the present invention. It should also be appreciated that the method described above may be supplemented with other methods for determining usage and be within the scope of the present invention. For example, the total accumulated time of usage may be recorded on EEPROM 36 and updated by microprocessor 43 from clock 46 and be utilized as an additional means for determining when catheter probe 22 has exceeded its recommended life.

Figure 5:
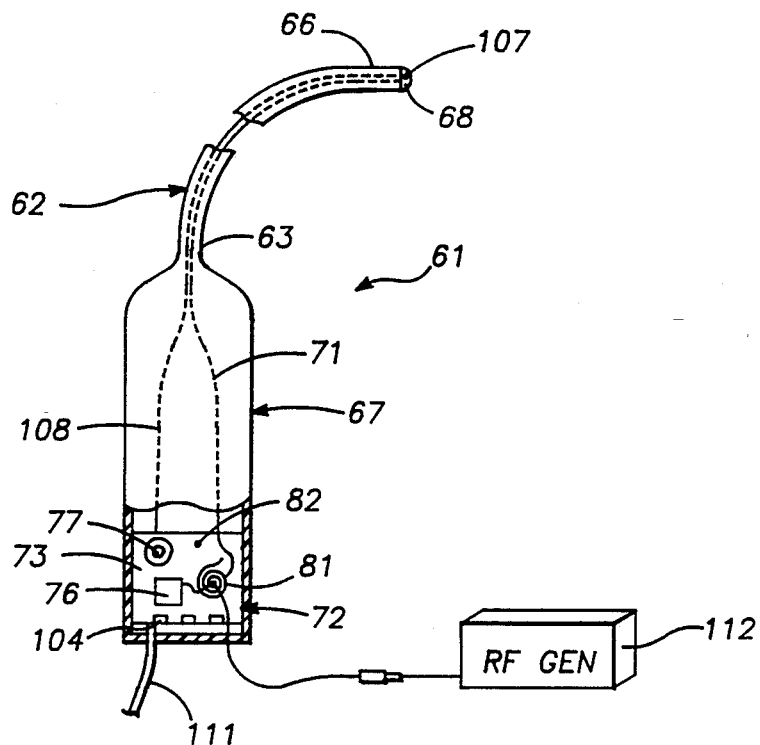
FIG. 5 is a perspective view of another embodiment of the medical device with usage memory of the present invention.

In another embodiment of the invention, a medical device 61 is provided which includes a flexible elongate member 62 having a proximal extremity 63 and a distal extremity 66 (See FIG. 5). A handle 67 is carried by proximal extremity 63. Proximal extremity 63 and handle 67 are adapted to be disposed outside of a human body and distal extremity 66 is adapted to be inserted into a body for performing an operation therein and includes a tip 68. Medical device 61 is of a type in which electrical energy is transmitted from handle 67 to distal extremity 66 and includes lead means in the form of wire 71 extending through flexible elongate member 62 from the handle to the distal extremity for carrying the electrical energy.

Handle 67 has a circuit or electronic module 72 which is embedded therein and includes a printed circuit board 73. A suitable microcontroller 76 such as a small 4-bit microcontroller of the type used in wristwatches is mounted on printed circuit board 73. Battery means in the form of a small battery 77 is also provided on printed circuit board 73 for serving as a power supply to microcontroller 76 and the other components on the printed circuit board. At least one sensing means is included within medical device 61 for sensing a parameter relating to each use thereof. As shown in FIG. 5, medical device 61 includes two sensing means on printed circuit board 73 in the form of an electrical sensor or printed coil 81 and a temperature sensor 82.

Figure 6:
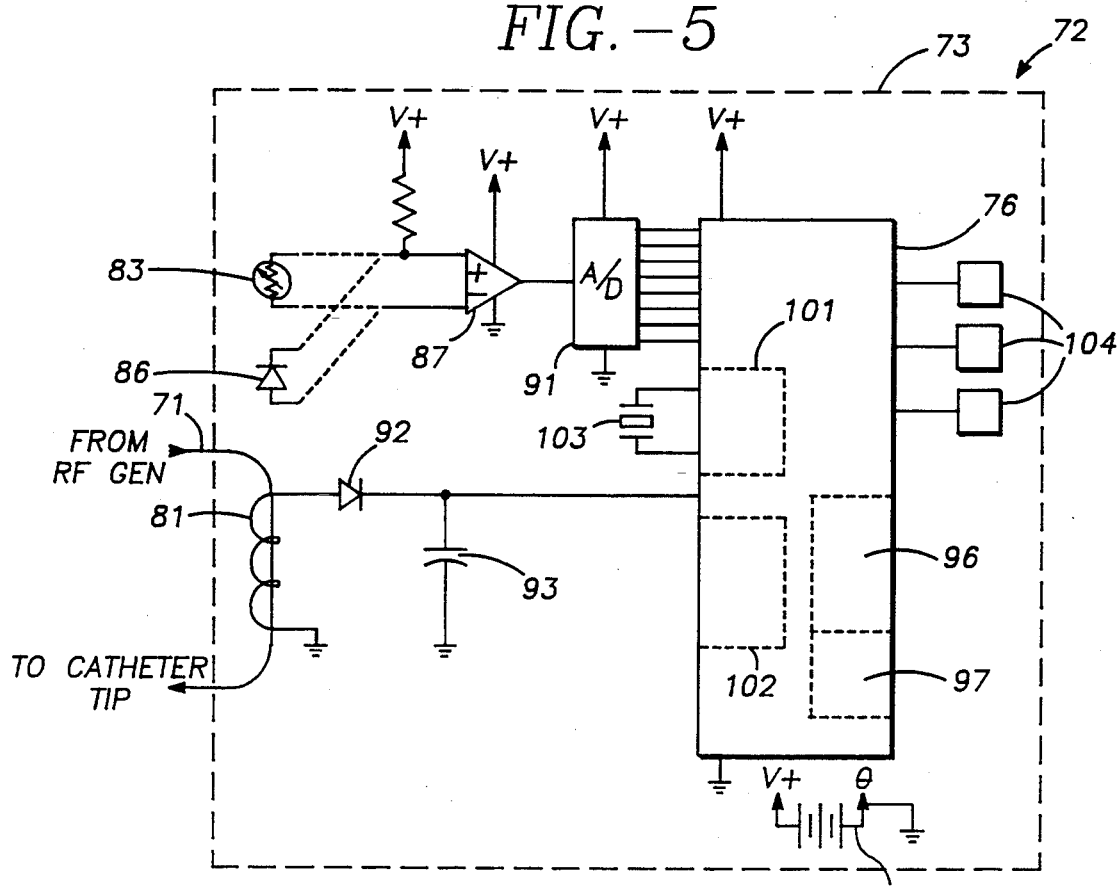
FIG. 6 is a diagram of the electronics for the usage memory of the medical device of FIG. 5.

Printed circuit board 73 and the electronics thereon are illustrated in more detail in FIG. 6. As shown therein, printed coil 81 and temperature sensor 82 are each electrically coupled to microcontroller 76 and generate an electrical signal with respect to each use of medical device 61 which is sent to the microcontroller. Temperature sensor 82 can be of any suitable type such as a thermistor 83 or a diode-type semiconductor sensor 86. The analog electrical signal generated by thermistor 83 or diode 86 is amplified by an amplifier 87 and converted to a digital signal by analog-to-digital converter 91 before going to microcontroller 76. Printed circuit board 73 is provided with a small hole (not shown) in the center of printed coil 81 through which wire 71 extends. Electrical energy traveling through wire 71 is detected by and induced into printed coil 81 by inductive coupling and is thereafter rectified by a diode 92 and filtered by a capacitor 93 to create a DC voltage level which travels to microcontroller 76.

At least one memory or recording means is carried by handle 67 for recording information relating to usage of medical device 61 as sensed by the sensing means carried thereby. More in particular, and as shown in FIG. 6, microcontroller 76 is provided with RAM 96 and EEPROM 97 therein. Microcontroller 76 further includes a real time clock 101 and a microprocessor 102. Circuit board 73 has a clock crystal 103 thereon which is coupled to microcontroller 76 for operating clock 101. At least three input/output pads 104 are included on circuit board 73 and are electrically coupled to microcontroller 76 for communicating with the microcontroller during manufacture thereof, for setting time clock 101 and for reading the contents of RAM 96 and EEPROM 97.

It should be appreciated that the sensing means of medical device 61 can be located other than on handle 67 and be within the scope of the present invention. For example, a temperature sensor 107 can be provided in tip 68 in addition to or in lieu of temperature sensor 82 and/or printed coil 81. Temperature sensor 107, which is shown in FIG. 5 but not in FIG. 6, is substantially similar to temperature sensor 82 and is electrically coupled to electronic module 72 by any suitable means such as wires 108 extending through flexible elongate member 62. Preferably, wires 108 are not associated with the function of tip 68 so as to be passive to the user of medical device 61.

Wires 111, one of which is shown in FIG. 5, are electrically connected to input/output pads 104 of printed circuit board 73 and extend external from handle 67. The proximal end of wire 71 is connected to a radio frequency generator 112 which serves as means for providing electrical energy to medical device 61 and, more in particular, to tip 68 thereof for any suitable purpose such as ablation.

In operation and use, temperature sensors 82 and 102 and printed coil 81 permit monitoring of the usage history of medical device 61 to evaluate the performance thereof and/or to ascertain whether the medical device is being used as recommended by the manufacturer and is within warranty. As can be appreciated by those in the art, medical device 61 is typically sterilized between uses. Monitoring of the sterilization cycles can be a method of determining the usage cycles of medical device 61. In this regard, temperature sensor 82 can be periodically polled by microprocessor 102 within microcontroller 76, for example for a few milliseconds every five minutes, to determine whether the temperature of medical device 61 has been elevated above a predetermined temperature programmed within microcontroller 76. This predetermined temperature should preferably be above ambient temperature and be high enough, such as 55° to 60° C., to indicate the occurrence of a sterilization cycle. Once the predetermined temperature has been detected by temperature sensor 82, microcontroller 76 records the time, date and duration of the sterilization cycle. Since sterilization cycles usually are several hours in duration, a five minute polling interval will be sufficient for detection thereof.

Printed coil 81 senses use of medical device 61 by detecting the application of radio frequency energy from radio frequency generator 112 to tip 68 for ablation purposes. As discussed above, application of such energy creates a DC voltage level which is sent to microcontroller 76. Upon receiving such an electrical signal, microcontroller 76 notes and records the time, date and duration of such ablation procedure.

Temperature sensor 107 in tip 68 monitors usage of medical device 61 by detecting a predetermined temperature above ambient temperature when tip 68 is inserted into a human body during an operation therein. Since a body's temperature is approximately 37° C. and the storage temperature of medical device 61 is approximately 20° C., microcontroller 76 can be programmed so that when tip 68 reaches a predetermined temperature which approaches 37° C., the periodic polling of temperature sensor 107 by microprocessor 102 triggers microcontroller 76 to record the time and date of such detection and the period of time during which the temperature of tip 68 remains above that predetermined temperature.

A detailed usage history detected by temperature sensors 82 and 107 and printed coil 81 and processed by microprocessor 102 is recorded on RAM 96 which is electrically coupled to the microprocessor within microcontroller 76. Critical information relating to usage history, for instance the number of sterilization cycles and the total number of radio frequency applications for ablation, is also be stored on EEPROM 97. As will be appreciated by those skilled in the art, information recorded on RAM 96 is lost once battery 97 goes dead. However, the information recorded on EEPROM 97 is retained thereon even after battery 77 goes dead. The information on both RAM 96 and EEPROM 97 can be externally accessed through input/output pads 104.

As can be seen, the sensing means of medical device 61 generate electrical signals relating to each use of the medical device for processing by microprocessor 102 within microcontroller 76. The processed usage information from microprocessor 102 is stored in RAM 96 and/or EEPROM 97. The monitoring system of medical device 61 is passive to the user in that it operates automatically and without need of activation by the user. The inclusion of battery 77 within handle 67 eliminates the need for a separate power supply for sensing, processing and recording the usage cycles of medical device 61 and permits such monitoring even when external power is not being supplied to medical device 61. The information recorded on RAM 96 and EEPROM 97 can be useful for ascertaining whether the medical device has been operated within the warranty and/or has exceeded the number of recommended uses. In addition, the usage history provides information on how medical device 61 is being used in the field. This information can assist the manufacturer of medical device 61 in its marketing, product development and/or manufacturing efforts.

In view of the foregoing, it can be seen that a new and improved method and device for automatically monitoring each use of a medical device has been provided. In the method and device, the number of uses is automatically recorded on the device and this usage information can be retained on the device when power thereto is shut off. The method and device can distinguish between usage cycles and operational steps during a usage cycle.

What is claimed is:

1. A reusable medical device for performing a medical procedure in a lumen in a body comprising a flexible elongate member having proximal and distal extremities, the distal extremity being adapted to be inserted into the lumen in the body for performing the procedure, the flexible elongate member having a length so that the proximal extremity is disposed outside the body when the distal extremity is in the body, at least one temperature sensor carried by the flexible elongate member for sensing a predetermined temperature relating to use of the medical device and generating an electrical signal, means secured to the proximal extremity including a microprocessor for receiving the electrical signal and recording information relating to use each time the temperature sensor reaches the predetermined temperature, means for recording in the microprocessor a maximum usage number and output means coupled to the microprocessor for providing an output when the maximum usage number has been exceeded.

2. A device as in claim 1 together with battery means carried by said proximal extremity which serves as a power supply for said microprocessor.

3. A device as in claim 1 wherein said temperature sensor is carried by said distal extremity for detecting a predetermined temperature above ambient temperature which corresponds to a temperature at the temperature sensor when the distal extremity is disposed in the lumen in the body.

4. A device as in claim 1 wherein said temperature sensor is carried by said proximal extremity for detecting a predetermined temperature above ambient temperature which corresponds to a temperature at the temperature sensor during sterilization of the medical device.

5. A system comprising a medical device for performing a medical procedure in a lumen in a body and means for monitoring usage cycle history of the medical device, the medical device including a flexible elongate member having proximal and distal extremities, the distal extremity of the medical device being adapted to be inserted into the lumen in the body for performing the procedure, the flexible elongate member having a length so that the proximal extremity is disposed outside the body when the distal extremity is in the body, a temperature sensor carried by the flexible elongate member and electrically coupled to the means for monitoring for sending a first electrical signal to the means for monitoring, lead means extending from the proximal extremity to the distal extremity for carrying electrical energy from the proximal extremity to the distal extremity, an electrical sensor carried by the flexible elongate member for detecting electrical energy passing through the lead means, the electrical sensor being electrically coupled to the means for monitoring for sending a second electrical signal to the means for monitoring, and at least one recording means disposed on the proximal extremity and electrically coupled to the means for monitoring, the means for monitoring receiving the electrical signals and recording information on the recording means each time the temperature sensor reaches a predetermined temperature above ambient temperature and each time electrical energy passes through the lead means, the recording means having output means for permitting access to the usage cycle history of the medical device.

6. A system as in claim 5 wherein said recording means includes an electrical erasable programmable read-only memory.

7. A system as in claim 5 wherein said means for monitoring is carried by said proximal extremity and wherein said system further includes battery means carried by the proximal extremity and electrically coupled to the means for monitoring for serving as a power supply thereto.

8. A system as in claim 5 wherein the temperature sensor is carried by the distal extremity for detecting a predetermined temperature above ambient temperature which corresponds to a temperature at the temperature sensor when the distal extremity is disposed in the lumen in the body.

9. A system as in claim 8 together with an additional temperature sensor carried by the proximal extremity and generating an additional electrical signal, the means for monitoring receiving the additional electrical signal and recording information on the recording means each time the additional temperature sensor reaches a predetermined temperature above ambient temperature which corresponds to a temperature at the additional temperature sensor during sterilization of the medical device.

10. A system as in claim 5 wherein said temperature sensor is carried by the proximal extremity for detecting a predetermined temperature above ambient temperature which corresponds to a temperature at the temperature sensor during sterilization of the medical device.

11. A reusable medical device for performing a medical procedure in a lumen in a body comprising a flexible elongate member having proximal and distal extremities, the distal extremity being adapted to be inserted into the lumen in the body for performing the procedure, the flexible elongate member having a length so that the proximal extremity is disposed outside the body when the distal extremity is in the body, a first temperature sensor carried by the proximal extremity and generating a first electrical signal and a second temperature sensor carried by the distal extremity and generating a second electrical sensor, lead means extending from the proximal extremity to the distal extremity for carrying electrical energy from the proximal extremity to the distal extremity, an electrical sensor carried by the flexible elongate member for detecting electrical energy passing through the lead means and generating a third electrical signal, means secured to the proximal extremity including a microprocessor for receiving the electrical signals and recording a usage history which includes each time the first temperature sensor reaches a first predetermined temperature above ambient temperature which corresponds to a temperature at the first temperature sensor during sterilization of the medical device, each time the second temperature sensor reaches a second predetermined temperature above ambient temperature which corresponds to a temperature at the second temperature sensor when the distal extremity is disposed in the lumen in the body and each time the third electrical signal is received from the electrical sensor, the microprocessor having output means for permitting access to the usage history of the medical device.

12. A device as in claim 11 together with battery means carried by said proximal extremity which serves as a power supply for the microprocessor.

* * * * *